United States Patent
Jakeman

(10) Patent No.: US 10,455,853 B2
(45) Date of Patent: Oct. 29, 2019

(54) NUTRITIONAL SUPPLEMENT COMPOSITION SUITABLE FOR IMPROVING LEAN TISSUE MASS STATUS IN AN ADULT HUMAN

(71) Applicant: UNIVERSITY OF LIMERICK, Limerick (IE)

(72) Inventor: Phil Jakeman, Birdhill (IE)

(73) Assignee: UNIVERSITY OF LIMERICK, Limerick (IE)

( * ) Notice: Subject to any disclaimer, the term of this patent is extended or adjusted under 35 U.S.C. 154(b) by 74 days.

(21) Appl. No.: 15/315,295

(22) PCT Filed: May 26, 2015

(86) PCT No.: PCT/EP2015/061607
§ 371 (c)(1),
(2) Date: Nov. 30, 2016

(87) PCT Pub. No.: WO2015/181181
PCT Pub. Date: Dec. 3, 2015

(65) Prior Publication Data
US 2018/0184700 A1   Jul. 5, 2018

(30) Foreign Application Priority Data
May 30, 2014   (EP) .................... 14170649

(51) Int. Cl.
| | | |
|---|---|---|
| A61K 38/01 | (2006.01) |
| A23L 33/19 | (2016.01) |
| A23L 33/00 | (2016.01) |
| A23L 33/155 | (2016.01) |
| A23L 33/18 | (2016.01) |
| A23L 33/16 | (2016.01) |
| A61P 21/00 | (2006.01) |
| A61K 9/00 | (2006.01) |
| A61K 31/593 | (2006.01) |
| A61K 33/06 | (2006.01) |
| A61K 38/17 | (2006.01) |

(52) U.S. Cl.
CPC .............. *A23L 33/19* (2016.08); *A23L 33/00* (2016.08); *A23L 33/155* (2016.08); *A23L 33/16* (2016.08); *A23L 33/18* (2016.08); *A61K 9/009* (2013.01); *A61K 31/593* (2013.01); *A61K 33/06* (2013.01); *A61K 38/018* (2013.01); *A61K 38/1709* (2013.01); *A61P 21/00* (2018.01); *A23V 2002/00* (2013.01)

(58) Field of Classification Search
None
See application file for complete search history.

(56) References Cited

U.S. PATENT DOCUMENTS

2007/0128252 A1 * 6/2007 Ward ..................... A23L 2/39
424/439

FOREIGN PATENT DOCUMENTS

| AU | 2011100139 A4 | 3/2001 |
| WO | 01/28356 A2 | 4/2001 |

OTHER PUBLICATIONS https://www.nutraingredients.com/Product-innovations/Optipep-clean-tasting-hydrolysed-whey-proteins referenced on Sep. 16, 2018. (Year: 2007).*
Kerksick et al., "Impact differing protein sources and a creatine containing nutritional formula after 12 weeks of resistance training", Nutrition 23(9): 647-656 (2007).
Rizzoli et al., "Dietary protein intakes and bone growth", International Congress Series 1297: 50-59 (2007).

* cited by examiner

*Primary Examiner* — Jessica Worsham
(74) *Attorney, Agent, or Firm* — Nixon Peabody LLP; David S. Resnick

(57) ABSTRACT

"A nutritional supplement composition suitable for improving lean tissue mass status in a mammal" A nutritional supplement suitable for increasing lean tissue mass in a mammal comprises protein, vitamin D, and calcium. The protein comprises a casein-based milk protein composition, a hydrolyzed whey-based milk protein composition having insulinotropic bioactivity, and a hydrolyzed whey-based milk protein composition having anti-oxidant bioactivity. The supplement increases lean tissue mass in a subject.

11 Claims, 4 Drawing Sheets

NUTRITIONAL SUPPLEMENT COMPOSITION SUITABLE FOR IMPROVING LEAN TISSUE MASS STATUS IN AN ADULT HUMAN

CROSS-REFERENCE TO RELATED APPLICATIONS

This Application is a 35 U.S.C. § 371 National Phase Entry application of International Application No. PCT/EP2015/061607 filed May 26, 2015, which designates the U.S., and which claims benefit of foreign priority under 35 U.S.C. § 119 of EP Application No. 14170649.9 filed on May 30, 2014, the contents of each of which are herein incorporated by reference in their entirety.

TECHNICAL FIELD

The invention relates to a nutritional supplement suitable for increasing lean tissue mass in a mammal, especially in an elderly human having less capacity for physical exercise. The invention also relates to a nutritional composition suitable for increasing lean tissue mass in a mammal and formulated as a single dose suitable for administration with a meal. The invention also relates to a non-therapeutic method of improving lean tissue mass or physical capacity in an elderly subject, and therapeutic methods for treating pathologies associated with lean tissue degradation in mammals.

BACKGROUND TO THE INVENTION

The Recommended Dietary Allowances (RDA) for different age groups reported by the Institute of Medicine in 2005 and the "safe levels" reported by the World Health Organization/Food and Agriculture Organization/United Nations University (WHO/FAO/UNU) in 2007 are based on analysis of available nitrogen balance studies. These reports state the mean protein requirement (EAR) to be 0.65 g of 'good-quality' protein per kg body mass per day and that the RDA or safe level of protein intake for both adult men and adult women is 0.83 g of 'good quality' protein per kg body mass per day and that the Acceptable Macronutrient Distribution Range (AMDR) for protein is 10-35% of total energy for adults. Though not universally accepted, there is considerable debate regarding the validity of the nitrogen balance approach to the determination of whole body protein requirement indicating that new research and novel research methodologies are necessary to establish whether the protein needs and optimal patterns of protein intake change with advancing age in adults.

It is well accepted that loss of body protein in aging (age-related sarcopenia) is associated with increased morbidity and mortality. The debate centres on whether protein intakes above the RDA have additional benefits for older adults, especially with respect to sarcopenia and osteoporosis. Recent metabolic and epidemiological studies suggest that the current recommendations of protein intake may not be adequate for maintenance of physical function and optimal health in older adults. Indeed, much of the recent evidence supports the contention that lean body mass can be better maintained if an older person consumes dietary protein at a level higher than the general RDA defined above. The RDA for protein from these meta-analyses tends towards higher protein intakes of 1.2 gram per kilogram body mass per day (approximating to 90 g for a 75 kg adult) to be evenly dispersed among the three main eating occasions, i.e. morning (breakfast, 30 g), mid-day (luncheon, 30 g) and evening (dinner, 30 g) meals. Of particular relevance, many of the studies for which protein supplements in the elderly have been used comprised isolates of the milk proteins, whey and casein.

Protein quality is judged by the essential amino acid (EAA) content and, therefore, an 'ideal' protein intake would be that which satisfies the daily requirements for EAAs, updated by the Institute of Medicine in 2005. Changes in muscle (lean tissue) mass occur in response to alterations in the balance between protein synthesis and degradation. Measured by post-prandial change in muscle protein synthesis (MPS) and protein breakdown (MPB), MPS increases within the immediate period (3-5 h) following ingestion of protein or AA mixture, the type of protein exerting different patterns and magnitude of stimulation of MPS. Proteins with a high relative EAA composition tend to stimulate MPS with a more consistent, positive effect. Milk proteins, whey and casein, are composed of approximately 50% EAAs and considered ideal proteins in this respect. As specific AA are now known to have unique physiologic effects beyond being constituents of protein that may further enhance MPS and accrual of lean tissue. Leucine is an essential amino acid known to induce a post-prandial increase in MPS. Leucine also acts as an insulin secretagogue. Insulin is seen as 'permissive' with respect to MPS, but a negative regulator of MPB, thereby augmenting net protein balance. Taking into account the arguments #1 and #2 above the most recent recommended, per-meal anabolic threshold of dietary protein/amino acid intake for older individuals is 25 to 30 g protein per meal, containing ~2.5 to 2.8 g leucine.

Muscle protein loss during aging may be partly explained by a decreased ability of ageing muscle to respond appropriately to protein/EAA/leucine intake. This defect mainly results from a decreased response and/or sensitivity of protein synthesis and degradation to leucine, ageing muscle being less responsive to the combined anabolic effect of elevated amino acid and insulin concentrations, mainly because of a reduced responsiveness of ageing skeletal muscle to these stimuli of muscle protein synthesis. Aging is also characterized by low grade inflammation, one of the components implicated in the development of sarcopenia. To this effect, antioxidant supplementation is able to improve the ability of leucine to stimulate protein synthesis in ageing muscle independently of an increase in leucine availability.

Rizzoli et al (INTERNATIONAL CONGRESS SERIES, EXCERPTA MEDICA, Vol. 1297, 1 Mar. 2007) is a review of bone growth in adolescence, and considers protein and calcium effects on the developing adult, and in particular the effects of nutrients on bine mass gain but not bone mass loss.

Kerksick et al (NUTRITION, ELSEVIER INC Vol. 23, No. 9, 2 Aug. 2007) describes a 12 week study of resistance (Rx) training versus no resistance training in which men (Mean age 27) were randomly assigned one of four (non-hydrolysed) milk protein+/−creatine supplements. The results show that RX alone can induce change in lean tissue mass and functional outcome independent of dietary/nutritional intervention. The reported body compositional outcome (Table 5) and change in functional outcome (Table 6) is a result of an interaction between resistance training and nutritional effect on lean tissue mass. Resistance training is unsuitable for many elderly patients.

It is an object of the invention to overcome at least one of the above-referenced problems.

STATEMENTS OF INVENTION

Broadly, the Applicant provides a nutritional supplement composition that when administered to a subject in at least two doses daily, and generally in two daily doses, with minor meals (i.e. the two daily meals with lowest protein content, for example breakfast or lunch), has been found to improve lean tissue mass status without the requirement for any accompanying resistance training or exercise regime, and improve bone quality. The composition comprises a major protein component, a minor vitamin D and calcium components. The major protein component comprises a casein-based milk protein composition (for example milk protein concentrate), a whey-based milk protein composition having insulinotropic bioactivity (for example, hydrolysed whey protein concentrate), and a whey protein composition having anti-oxidant bioactivity (for example, hydrolysed whey protein isolate). Table 6 below shows the change (A) in lean tissue mass (LTM) after 24 weeks of control (CON; isoenergetic, non-protein) or composition of the invention (FORM) supplementation in 50-70 year olds, in which the composition of the invention resulted in an increase in LTM. Table 7 below shows the change in bone mineral density (BMD) and biomarker of bone resorption (CTx) after 24 weeks of control (CON; isoenergetic, non-protein) or composition of the invention (FORM) supplementation in 50-70 year olds, in which the composition of the invention resulted in an increase in site-specific areal BMD and reduction in CTx.

In a first aspect, the invention provides a nutritional supplement composition suitable for improving lean tissue mass status in an adult human, the composition comprising a protein component, vitamin D and calcium; in which the protein component comprises a casein-based milk protein composition; a whey-based milk protein composition having high or augmented insulinotropic bioactivity; and a whey-based milk protein composition having high or augmented antioxidant bioactivity.

In this specification, the term "high or augmented insulinotropic bioactivity" as applied to a composition should be understood to mean that the composition has an insulin secretion activity of at least 20, 26 or 30 ng per mg composition as determined in the in-vitro insulin secretion assay described below.

In this specification, the term "high or augmented anti-oxidant bioactivity" as applied to a composition should be understood to mean that the composition has an oxygen radical absorbance capacity (ORAC) of at least 60,000, 70,000, 80,000 μmol TE/100 g material as determined in the in-vitro antioxidant activity assay described below.

In this specification, the term "nutritional supplement composition" or "supplement composition" or "nutritional composition" should be understood to mean something that is ingested by a human, generally with a meal, for example a nutritional supplement in solid or liquid form. In one preferred embodiment, the supplement is provided in the form of a particulate product, such as a powder, that is typically intended to be dissolved or dispersed in water and ingested as a drink. In other embodiments, the supplement is provided in the form of a snack, for example a snack food bar. In other embodiments, the supplement may be provided in the form of a unit dose product, for example a tablet. In other embodiments, the supplement is provided in the form of a particulate product, such as a sachet of powder, that is typically intended to be sprinkled over food prior to consumption.

Typically, at least one and preferably both of the whey-based milk protein compositions comprise or consists of a hydrolysate.

Typically, the supplement composition comprises (per 100 g dry weight) at least 60 g protein, 0.01 to 0.1 mg vitamin D, and 1 to 5 g calcium, and in which the protein component of the supplement composition typically comprises:
  50-60 g of a casein-based milk protein composition,
  5-15 g of a first hydrolysed whey-based milk protein composition having high or augmented insulinotropic bioactivity; and
  4-8 g of a second hydrolysed whey-based milk protein composition having high or augmented antioxidant bioactivity.

The term "casein-based milk protein composition" should be understood to mean a milk protein concentrate in which at least 70% of the protein is casein. Examples are skim-milk or whole milk concentrates. The term "50-60 g of a casein-based milk protein composition" should be understood to mean an amount of the casein-based milk protein composition that provides 50-60 g protein. As described above, one suitable casein-based milk protein composition is MPC-80, a spray-dried powder prepared from skim milk and having 80% protein. As shown in Table 1 below, one composition of the invention comprises 68.15 g MPC-80 per 100 g composition dry weight, which approximates to 54.5 g protein per 100 g composition dry weight.

The term "first hydrolysed whey-based milk protein composition having high or augmented insulinotropic bioactivity" should be understood to mean an enzymatically hydrolysed whey-based milk protein composition, typically having a degree of hydrolysis of 30-35, 31-33, and ideally 32% DH. The term "5-15 g of a first hydrolysed whey-based milk protein composition" should be understood to mean an amount of the first hydrolysed why-based milk protein composition that provides 5-15 g protein. As described above, one suitable hydrolysed whey-based milk protein composition is OPTIPEP, a powder having 78% protein. As shown in Table 1 below, one composition of the invention comprises 15.53 g OPTIPEP per 100 g composition dry weight, which approximates to 12.11 g protein per 100 g composition dry weight.

The term "second hydrolysed whey-based milk protein composition having high or augmented anti-oxidant bioactivity" should be understood to mean an enzymatically hydrolysed whey-based milk protein composition, typically a whey protein isolate, typically having a degree of hydrolysis of 42-47, preferably 44-46, and ideally about 45% DH. The term "4-8 g of a second hydrolysed whey-based milk protein composition" should be understood to mean an amount of the second hydrolysed why-based milk protein composition that provides 4-8 g protein. As described above, one suitable hydrolysed whey-based milk protein composition is CVH-15, a hydrolysed whey protein isolate powder having 84% protein. As shown in Table 1 below, one composition of the invention comprises 7.21 g CVH-15 per 100 g composition dry weight, which approximates to 6.06 g protein per 100 g composition dry weight.

Suitably, the protein component of the supplement composition comprises:
  52-56 g of a casein-based milk protein composition,
  11.7-12.5 g of the first hydrolysed whey-based milk protein composition; and
  5.8-6.2 g of the second hydrolysed whey-based milk protein composition.

Preferably, the supplement composition comprises:
  60-80 g of the protein component;
  2-4 g calcium; and
  0.04-0.07 mg vitamin D.

Preferably, the supplement composition comprises
67-73 g of the protein component;
2.5-3.0 g calcium; and
0.05-0.06 mg vitamin D.

In this specification, the term "dry weight" should be understood to mean a powder having 4-6% moisture, preferably 5% moisture.

Typically, both the whey-based milk protein composition having high or augmented insulinotropic activity and the milk protein composition having high or augmented antioxidant activity are formed in a process that involves hydrolysis, ideally enzymatic hydrolysis, of whey Typically, the supplement composition comprises at least 60%, 65% or 70% protein (wt/wt).

Typically, the supplement composition comprises 0.01 to 0.1 mg, 0.03 to 0.07 mg, or 0.05 to 0.07 mg, Vitamin D per 100 g composition (hereafter "mg/100 g Vitamin D")

Typically, the supplement composition comprises 1 to 5 g, 2 to 4 g, or 2.5-3 g calcium per 100 g composition (hereafter "g/100 g calcium"). Ideally the calcium is milk-derived, ideally bovine milk-derived calcium.

Typically, the supplement composition comprises at least 60% protein, 0.01-0.1 mg/100 g vitamin D, and 1-5 g/100 g calcium. Suitably, the supplement composition comprises 70-75% protein (wt/wt), 0.03 to 0.07 mg/100 g vitamin D, and 1 to 4 g/100 g calcium. Ideally, the supplement composition comprises 70-73% protein, about 0.05 to 0.06 mg/100 g vitamin D, and 2 to 3 g/100 g calcium.

Preferably, the essential amino acid (i.e. those amino acids that are not synthesised by the body and, therefore need to be provided in the diet) content of the protein in the supplement composition is at least 40 g/100 g, 41 g/100 g, 42 g/100 g, 43 g/100 g, 44 g/100 g, 45 g/100 g, or 46 g/100 g protein. Preferably, the protein comprises at least 1.5 g of the following essential amino acids per 100 g protein, leucine, isoleucine, lysine, methionine, phenylalanine, threonine, valine and histidine.

Typically, the supplement composition has an insulin secretion activity of at least 20, 21, 22, 23 or 24 ng per mg protein as determined in the in-vitro insulin secretion assay described below.

Suitably, the supplement composition has an oxygen radical absorbance capacity (ORAC) of at least 20,000, 25,000, 27,000, or 28,000 μmol TE/100 g of formulated powder as determined in the in-vitro antioxidant activity assay described below.

Suitably, the calcium component of the supplement composition comprises milk-derived calcium, for example in one embodiment, the calcium is sourced from Glanbia under the registered tradename TruCal®. Typically, the supplement composition comprise 1-4%, 2.5-3.0%, and ideally about 2.78% calcium (wt/wt).

Typically, the supplement composition is provided in the form of a powder, although other particulate forms are envisaged such as, for example flakes, pellets and the like. Suitably, the supplement composition is soluble in water.

The invention also provides a supplement composition of the invention and provided in the form of a single dose suitable for administration with a meal, and comprising 8 to 17 g protein, 6 to 13 μg vitamin D, and 250 to 500 mg calcium per dose.

Exemplary unit dose compositions comprise:
about 8 g protein, about 6 μg vitamin D, and about 250 mg calcium;
about 10 g protein, about 9 μg vitamin D, and about 300 mg calcium;
about 12 g protein, about 10 μg vitamin D, and about 350 mg calcium;
about 14 g protein, about 11 μg vitamin D, and about 400 mg calcium; or
about 16 g protein, about 12 μg vitamin D, and about 450 mg calcium.

The single dose is typically provided as a powder in a sachet. In one embodiment, two sachets are provided as a single package unit with a tear line dividing the two sachets.

The invention also provides a comestible composition, for example a food or beverage, comprising the supplement composition of the invention.

The supplement compositions of the invention have therapeutic and non-therapeutic uses. In one embodiment, the compositions of the invention may be employed non-therapeutically to improve lean tissue mass status in an elderly healthy subject or to improve physical capacity in a subject, typically a healthy subject, and generally an elderly healthy subject.

The supplement composition of the invention may be employed non-therapeutically to improve bone status in a subject, typically a healthy subject, and generally an elderly healthy subject. The term "bone status" should be understood to mean bone protein content, bone protein quality, or bone mineral content.

In a preferred embodiment, the invention relates to a method of improving lean tissue mass, bone status, or lean tissue mass and bone status, in a subject comprising the step of administering a supplement composition to the subject.

In another embodiment, the compositions of the invention may be employed therapeutically to prevent or treat a disease or condition associated with lean tissue mass degradation or deficit in a subject of any age, especially elderly subjects, or to treat physical incapacity in a subject of any age, especially elderly subjects, or to treat or prevent bone degeneration (due to reduced bone protein or mineral content) in a subject of any age, especially elderly subjects.

The supplement compositions of the invention are typically administered over a period of 12 to 48 weeks, ideally over a period of at least 24 weeks.

Thus, in one aspect, the invention provides a non-therapeutic method of improving lean tissue mass status in a mammal, comprising the step of administering a supplement composition according to the invention to the mammal, typically in two doses daily, in which each of the two doses is administered with a separate minor meal.

The term "improving lean tissue mass status" should be understood to mean increasing lean tissue mass, or inhibiting or preventing the rate of lean tissue mass degradation.

The term "minor meal" should be understood to mean those meals that have the lowest protein content, whereby the protein intake in the meal is sub-optimal, i.e. <30 g. Thus, when a person takes their main meal of the day in the evening time, the minor meals would be breakfast and lunch.

The invention also provides a non-therapeutic method of improving physical capacity in a mammal, comprising the step of administering a food supplement according to the invention to the mammal in two doses daily, in which each of the two doses is administered with a separate minor meal.

The term "physical capacity" should be understood to mean the facility or power to produce, perform, or deploy the body's locomotor ability (muscle strength and balance) in a variety of ways to allow an individual to perform activities of daily living and enhance overall quality of life.

The invention also provides a supplement composition according to the invention, for use in a method of preventing or treating a disease or condition associated with lean tissue mass degradation in a mammal, in which each of the two doses is typically administered with a separate minor meal. Suitably, the disease or condition is sarcopaenia.

The invention also provides a supplement composition according to the invention, for use in a method of preventing or treating a disease or condition associated with reduced bone mineral or protein content, in a mammal, in which each of the two doses is typically administered with a separate minor meal. Suitably, the disease or condition is selected from sarcopaenia osteoporosis.

The invention also provides a non-therapeutic method of improving bone protein content or bone protein quality in a mammal, comprising the step of administering a supplement composition according to the invention to the mammal, typically in two doses daily, in which each of the two doses is administered with a separate minor meal.

The term "bone protein content" should be understood to mean that approximately 30% of bone is composed of organic compounds, of which 90 to 95% is in the form of the protein Type I collagen which provides a structural framework for connective tissues and plays a central role in the formation of new bone from progenitors.

The term "bone quality" should be understood to mean bone protein quality or bone mineral density.

The term "bone protein quality" should be understood to provide information not only about Bone Mineral Density (BMD) or Bone Mineral Content (BMC) but also about architecture and elasticity. Bone quality refers, in part, to the organic matrix of bone but also describes a set of characteristics that influence strength such as architecture, remodelling and damage accumulation (ref: National Institute of Health, Osteoporosis prevention, diagnosis and therapy, NIH Consensus Statement 17 (2000), 1-45.)

In particular, the invention relates to a method (therapeutic or non-therapeutic) for inhibiting or preventing loss of LTM in an elderly subject comprising administering to the elderly subject a supplement composition according to the invention, ideally in two doses daily, in which each of the two doses is administered with a separate minor meal. Typically, each dose comprises 8 to 17 g protein, 6 to 13 µg vitamin D, and 250 to 500 mg calcium per dose.

Exemplary unit dose compositions comprise:
about 8 g protein, about 6 µg vitamin D, and about 250 mg calcium;
about 10 g protein, about 9 µg vitamin D, and about 300 mg calcium;
about 12 g protein, about 10 µg vitamin D, and about 350 mg calcium;
about 14 g protein, about 11 µg vitamin D, and about 400 mg calcium; or
about 16 g protein, about 12 µg vitamin D, and about 450 mg calcium.

The term elderly subject should be understood to mean a human that is at least 50 years of age, and ideally 50-75 years of age.

The term "about" as employed herein means the stated dose+/−10%.

DETAILED DESCRIPTION OF THE INVENTION

Manufacture of Composition of the Invention

Figure 1:
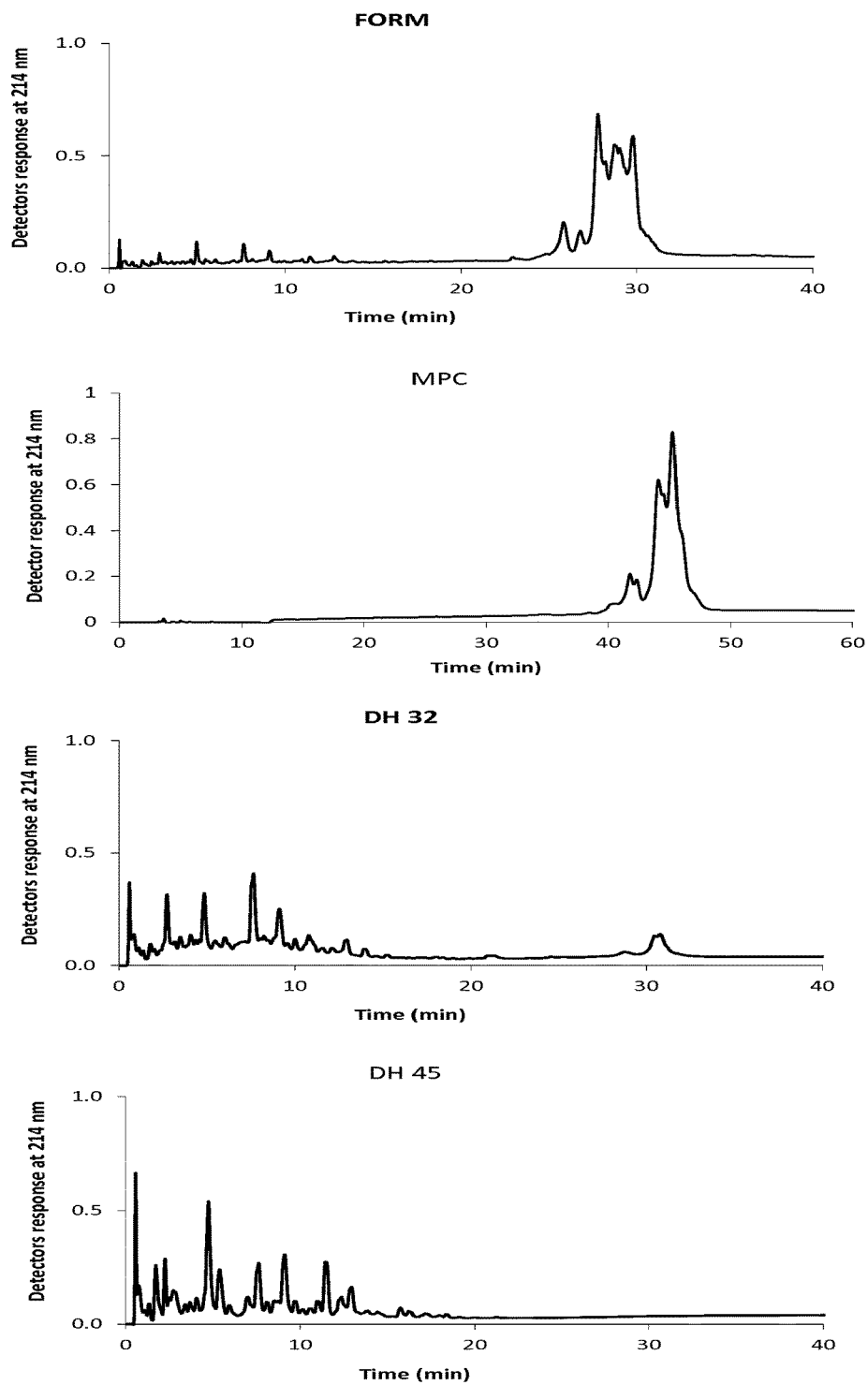
FIG. 1—Reverse phase ultra-performance liquid chromatography profile of the nutrient formulation (FORM), milk protein concentrate (MPC), whey protein hydrolysate degree of hydrolysis 32% (DH 32), whey protein hydrolysate degree of hydrolysis DH 45% (DH 45).

All the active ingredients (MPC, CVH 15, Optipep 80, Trucal, Vit D3) in Table 1 below were blended with flavours and instantised.

TABLE 1

| Ingredient | Composition g/100 g | Active substance | Specified amount g/100 g |
|---|---|---|---|
| CVH-15 (84% protein) | 7.120 | Protein from CVH | 6.058 |
| MPC-80 (80% protein) | 68.155 | Protein from MPC | 54.524 |
| Trucal | 9.077 | Calcium from milk | 2.178 |
| OPTIPEP 80% (78% protein) | 15.534 | Protein from OPTIPEP | 12.117 |
| Vitamin D3 (cholecalciferol) 0.25% | 0.0230 | D3 (Cholecalciferol) | 0.0000575 |

Method for Determining Degree of Hydrolysis (% DH) of Whey Protein Formulations

The degree of hydrolysis (DH) of hydrolysed milk proteins was calculated using the TNBS assay (Adler-Nissen 1979) and as modified by Spellman et al. (2003). A 5% TNBS solution was diluted to 0.1% in 212.5 mM sodium phosphate buffer, pH 8.2. Hydrolysate samples and Leu standards were diluted (as appropriate) in 1% (w/v) SDS solution and heated to 50° C. for 30 min in a water bath. Diluted samples or Leu standards (125 µL) were added to 1 mL of 212.5 mM sodium phosphate buffer, pH 8.2 and 1 mL of 0.1% TNBS solution. Samples were vortex mixed and incubated at 50° C. for 1 h, in the dark. The reaction was stopped by addition of 2 mL 0.1 M HCl. The absorbance at 340 nm was determined using a spectrophotometer (Shimadzu UV-mini 1240, Kyoto, Japan). All samples and Leu standards were assayed in triplicate.

The amino nitrogen content of each sample was determined from a Leu calibration curve (0-56 mg/L). The DH was calculated using the formula;

$$DH\ (\%) = 100 \times (AN2 - AN1/Nbp)$$

where: AN1 and AN2 are the amino nitrogen content of the protein substrate prior to and post hydrolysis (mg/g protein), respectively. Nbp is the nitrogen content of the peptide bonds in the protein substrate, 112.1 and 123.3 (mg/g protein) for CN and WP, respectively.

Physiochemical Characteristics

Reverse Phase Ultra Performance Liquid Chromatography

Intact and hydrolysed WP samples were analysed by reverse phase ultra performance liquid chromatography (RP-UPLC) as described by Nongonierma and FitzGerald (2012). The UPLC system (Acquity UPLC®, Waters, Milford, Mass., USA), comprising of binary solvent and auto sample manager, a heated column compartment and TUV absorbance detector. The pump was operated at a flow rate of 0.3 mL/min and 1 μL of each sample was injected onto the column. Separation of proteins and peptides was carried out at 30° C. using a 2.1×50 mm, 1.7 μm Acquity UPLC C18 BEH column (Waters) fitted with a pre-column security guard (VanGuard, Waters). The system was interfaced with Empower 2 (Waters) data handling software. Mobile phase A consisted of 0.1% (v/v) TFA in HPLC grade water. Mobile phase B was 0.1% (v/v) TFA in 80% HPLC grade ACN in HPLC grade water. Freeze dried intact and hydrolysed protein material were diluted to a concentration of 0.8% (w/v) in mobile phase A and were filtered through 0.2 μm filters (Phenomenex, Phenex RC, Cheshire, UK) prior to injection. The gradient elution program used to separate the proteins and peptides consisted of a linear gradient 0-0.3 min 0% B; 0.3-45 min 0-80% B; 45-46 min 80-100% B; 46-48 min 100% B; 48-49 min 100-0% B, 49-51 min 0% B. The absorbance of the eluent was monitored at 214 nm.

Gel Permeation Chromatography

Molecular mass distribution profiles of the intact and hydrolysed milk proteins were obtained as per the methodology described by Spellman et al., (2005). A gel permeation chromatography (GPC) system (Waters) comprising of a binary pump (Waters, 1525), dual absorbance detector (Waters, 2487) and an autosampler (Waters 717 Plus) was utilised. Separation was by isocratic elution with 0.1% TFA in 30% HPLC grade ACN at a flow rate of 0.5 mL/min and 20 μL of sample was injected. Each sample was prepared at a concentration of 0.25% (w/v) in 0.1% TFA, 30% (v/v) HPLC grade ACN and pre-filtered through 0.2 μm polytetrafluoroethylene filters (VWR, Dublin, Ireland). Separation of proteins and peptides were carried on a TSK-Gel G2000SW column (10 μm Particle size, 600 mm×7.5 mm, ID; Tosoh Biosciences, Tokyo, Japan) connected to TSK-Gel G2000SW guard column (10 μm, 50 mm×7.5 mm ID; Tosoh Biosciences). The detector response was monitored at 214 nm and the total run time was 60 min (FIG. 1). The system was calibrated using protein, peptide and amino acid standards with a molecular mass between 67500 and 218 Da including BSA (67500 Da), β-Lg (36000 Da), α-La (14200 Da), Cytochrome c (12300 Da), aprotinin (6500 Da), bacitracin (1400), Leu-Trp-Met-Arg (604 Da), Asp-Glu (262 Da) and Tyr-HCl (218 Da). The calibration curve was prepared from the average retention time (n=3) of each standard plotted against the Log of the molecular mass of each standard. The system was interfaced with Breeze Software (Waters) for data analysis. Data for each hydrolysate sample was expressed as percentage area within a defined molecular mass range for each chromatogram obtained at 214 nm (Table 2)

TABLE 2

Molecular mass distribution profile for nutrient formulation (FORM), intact milk protein concentrate (MPC) and whey protein hydrolysates degree of hydrolyis (DH) from 4 to 45%.

| Compound | Molecular Mass Distribution (% area)* | | | |
|---|---|---|---|---|
| | >5 kDa | 5-1 kDa | 1-0.5 kDa | <0.5 kDa |
| FORM | 87.1 | 2.6 | 0.1 | 10.3 |
| Intact MPC | 97.6 | 1.4 | 0 | 0 |
| WPC DH 32 | 19.6 | 9.7 | 16.6 | 54.1 |
| WPI DH 45 | 0.3 | 10.3 | 17.1 | 72.3 |

*Values expressed as % area within a defined molecular mass range for a gel permeation chromatogram obtained at 214 nm.

Total Amino Acid Analysis

Complete acid hydrolysis of intact and hydrolysed whey proteins was performed using 6 M HCl at 110° C., for 23 h. All samples were deproteinised by mixing with equal volumes of 24% trichloroacetic acid. After 10 min samples were centrifuged (Beckman Coulter, Allegra X-22R) at 10000 rpm for 10 min. The supernatant removed for analysis and diluted with 0.2 M sodium citrate buffer, pH 2.2. Amino acids were quantified using a Joel JLC-500/V amino acid analyser (Joel (UK) Ltd., Herts, UK) fitted with a Joel Na+ high performance cation-exchange column. Norleucine was used as an internal standard (Table 3).

TABLE 3

Analysis of EAAs as g/100 g of the composition and per 100 gram of protein contained within the 100 g of formulated powder

| Amino Acid | Per 100 g Powder | Per 100 g Protein |
|---|---|---|
| Alanine | 2.49 | 3.43 |
| Arginine | 2.14 | 2.95 |
| Aspartic acid | 5.49 | 7.55 |
| Cystine | 1.06 | 1.46 |
| Glutamic acid | 13.77 | 18.94 |
| Glycine | 1.19 | 1.64 |
| Histidine | 1.98 | 2.72 |
| Isoleucine | 3.56 | 4.90 |
| Leucine | 6.60 | 9.08 |
| Lysine | 5.33 | 7.34 |
| Methionine | 2.08 | 2.86 |
| Phenylalanine | 2.99 | 4.11 |
| Proline | 5.87 | 8.08 |
| Serine | 3.51 | 4.83 |
| Threonine | 3.36 | 4.62 |
| Tryptophan | n/a | n/a |
| Tyrosine | 2.70 | 3.71 |
| Valine | 4.42 | 6.08 |
| ΣEAA | 34.08 | 46.88 |
| Σ AA | 68.56 | 94.30 |
| % AA as EAA | | 49.7% |

Bioactivity Analysis:

In Vitro Insulin Secretion by Pancreatic β-Cell

Figure 2:
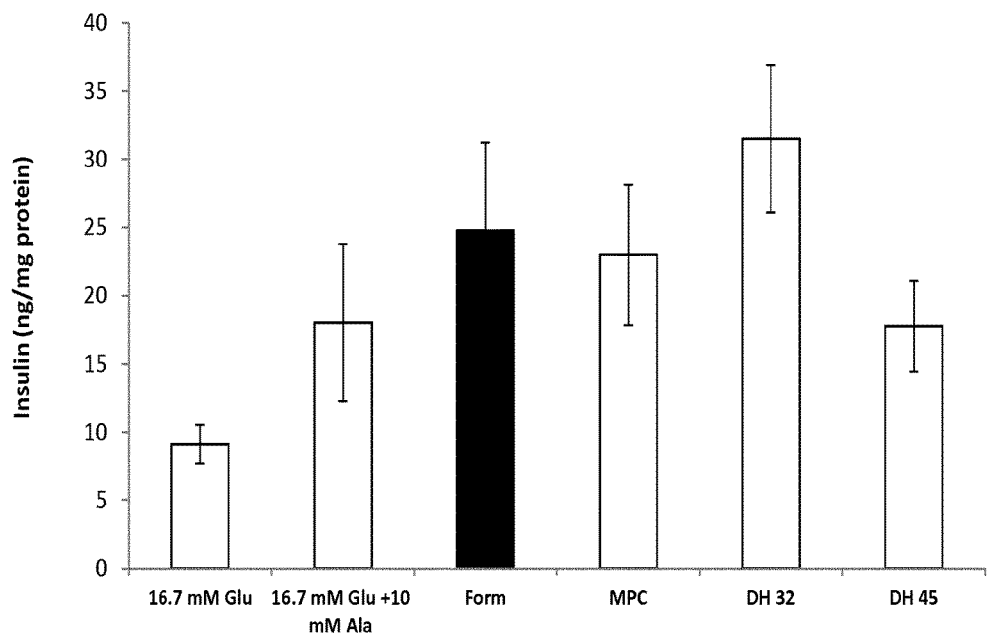
FIG. 2—In vitro insulin secretion from BRIN BD11 β-cells for the glucose control, positive control glucose plus alanine, nutrient formulation (FORM), milk protein concentrate (MPC), whey protein hydrolysate degree of hydrolysis 32% and whey protein hydrolysate degree of hydrolysis 45%. A 1 mg/ml solution of each test compound was applied to the cells. Values represent the mean±SD, n=4.

Pancreatic BRIN BD11 β-cells were used to measure acute insulin secretion (Kiely et al. 2007). Cells were maintained in RPMI-1640 tissue culture medium supplemented with 10% (v/v) foetal bovine serum, 0.1% antibiotics (100 U/mL penicillin and 0.1 mg/mL streptomycin) and containing 11.1 mM glucose, 0.1% Gln, pH 7.4. Cells were seeded into a 6-well microplate (83.1839, Sarstedt), incubated (Forma Scientific) with 5% $CO_2$ and 95% air at 37° C. and allowed to adhere overnight. Cells were then washed with phosphate buffer saline before being incubated in Krebs-Ringer bicarbonate buffer, at pH 7.4 containing 1.1 mM glucose. After 40 min of incubation the buffer was removed. Hydrolysates samples were applied to the cells at a concentration of 1 mg/mL in Krebs ringer buffer, containing 16.7 mM glucose, for 20 min. The supernatant was then removed and acute insulin secretion was measured by ELISA. Ala at 10 mM was used as a positive control (FIG. 2).

Oxygen Radical Absorbance Capacity (ORAC) Assay

Figure 3:
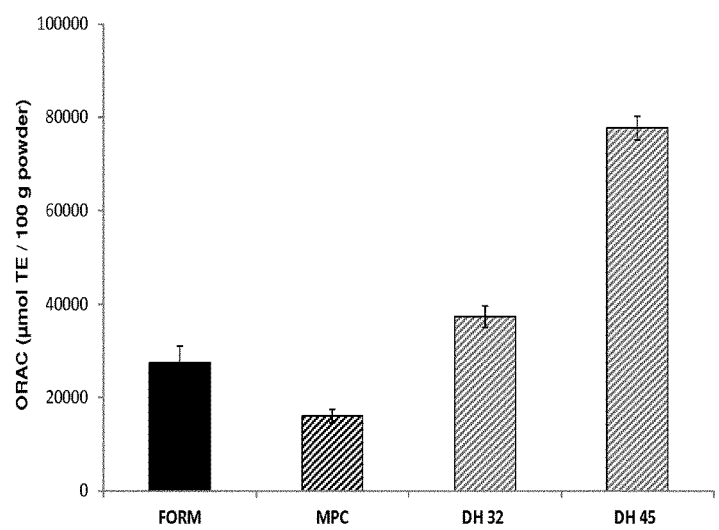
FIG. 3—Oxygen radical absorbance capacity (ORAC) values of the nutrient formulation (FORM), intact milk protein concentrate (MPC), whey protein hydrolysates degree of hydrolysis (DH) 32% and DH 45%. Values are expressed as µmol of Trolox equivalent per 100 g of powder (µmol TE/100 g powder) and represent the mean±SD, n=3.

Antioxidant capacity was evaluated using the fluorescence based ORAC assay as per the methodology of Harnedy and FitzGerald, (2013) with some modifications. The assay was performed in a 96 well microplate (Fisher Scientific, Dublin, Ireland). A Trolox standard curve was generated by assaying Trolox standards at concentrations between 10 and 200 μM. Test samples, blank (assay buffer) and Trolox standards were dissolved in 75 mM sodium phosphate buffer, pH 7.0 and were added (50 μL) to the appropriate wells and pre-incubated with 50 μL of 0.312 μM fluorescein (final concentration) at 37° C. for 10 min in a microplate reader (Biotek Synergy HT, Winooski, USA). Baseline fluorescence was measured at excitation (485 nm)

and emission (520 nm) wavelengths after 1 min. The reaction was initiated by addition of 25 µL of 44.2 mM AAPH (final concentration) to each well. The microplate was incubated at 37° C. for 120 min during which fluorescence was measured every 5 min. For each sample, the reaction was deemed to be complete if final fluorescence intensity (FIn) was less than 5% of initial fluorescence (FI0). Final results were presented as µmol TE per 100 g of dry weight (µmol TE/100 g dw) (FIG. 3). All data are presented as the mean±SD of independent triplicate analyses (n=3).

C. In-Vivo Studies

Study Design

All procedures were in accordance with the Faculty of Education & Health Sciences Research Ethics Committee (EHSREC10/45), University of Limerick.

Figure 4:
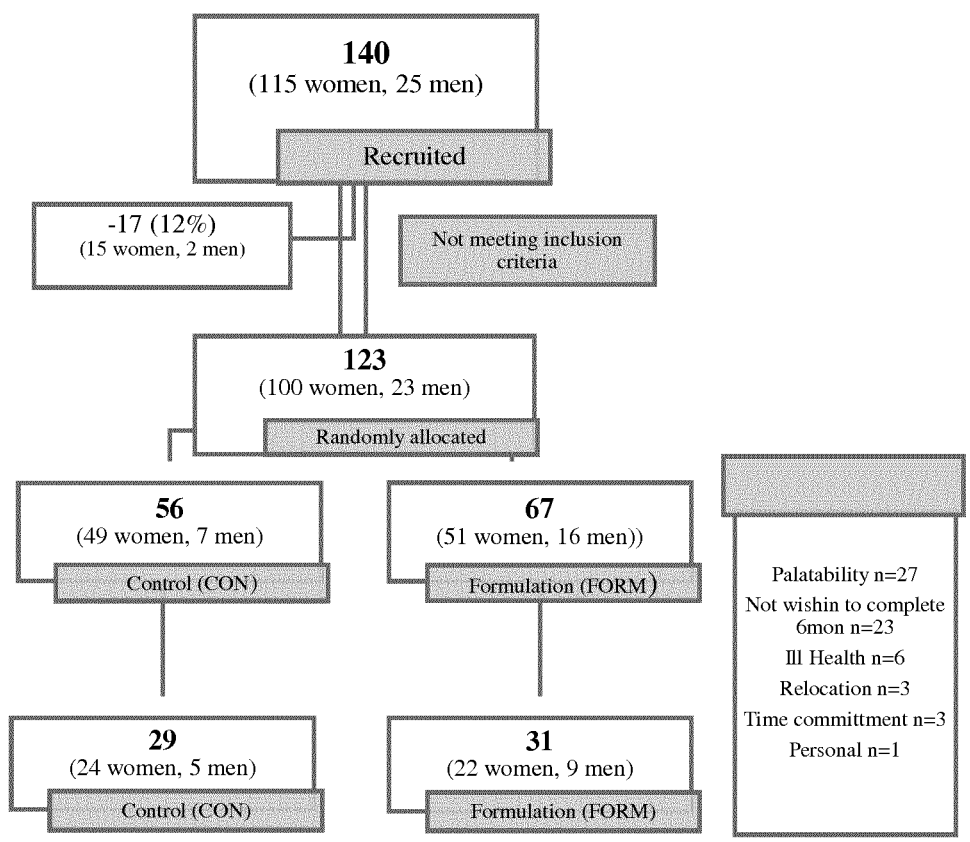
FIG. 4. In-vivo study design and flowchart

24-week randomised, single blind, control trial of healthy adult women and men aged 50-70 y. A convenience sample of 140 healthy adult women and men aged 50-70 y were recruited through email invitation and by word-of-mouth. Eligible participants were screened by a medical doctor and provided a full medical history. Those defined as healthy, i.e. disease-free based on Grieg et al. 1994, independent-living and willing to consume a nutrient supplement to their habitual diet, twice per day (bd. (bi-daily)) for 24 weeks (6 month) were invited to participate and to provide written, informed consent. On entry to the study participants were randomly assigned to receive a food supplement containing either a maltodextrin control (CON) or isoenergetic milk-protein based formulation (FORM). Completion of a 4-day dietary intake record and body compositional analysis preceded the 24 week intervention (FIG. 4).

Body Composition

Height was measured to the nearest 0.1 cm using a stadiometer (Seca, Birmingham, UK) and body mass to the nearest 0.1 kg (Tanita MC-180MA Body Composition Analyser, Tanita UK Ltd.). A Lunar iDXA™ scanner (GE Healthcare, Chalfont St Giles, Bucks., UK) with enCORETM v.14.1 software was used to capture total body scans and site specific scans of the hip and lumbar region for measurement of bone mineral density (BMD). The precision (root mean square coefficient of variance (RMS-CV)) of the iDXA for repeated measures of lean tissue mass on 87 subjects (age 35±17.6 years, range 18-71) was 0.6% as per ISCD recommendations (Baim et al 2008).

Statistical Analysis

Statistical analyses were performed using PASW Statistics 20.0 for Windows (SPSS, Inc., Chicago, Ill.). Statistical significance (two-tailed) was set at $P<0.05$ for all analyses. All data was tested for normality and homoscedasticity using Shapiro-Wilk and Levene's test respectively. Mean and the standard deviation (SD), median and interquartile range (IQR) are reported for baseline descriptive statistics. Differences between groups at baseline was analysed using an independent t-test for parametric data and Mann Whitney U test for non-parametric data. The dependent variable (24-week change in lean tissue mass ($\Delta$LTM)) was found to be normally distributed and was analysed using a univariate two-way ANOVA with treatment group and gender defined as fixed factors. The treatment effect was additionally analysed by two-way ANCOVA with group and gender as fixed factors, with baseline value of the dependent variable as a covariate. P values are described for the corrected model unless otherwise stated, with corresponding power (1–ß).

Subject Recruitment:

140 volunteers (115 women, 25 men), aged 50-70 y were recruited and agreed to participate in the study. 17 (15 women, 2 men; ~12%) were excluded following medical screening. The remaining 123 subjects were randomly assigned to either CON (49 women, 7 men) or FORM (51 women, 16 men) (FIG. 4).

Baseline Dietary Analysis:

Baseline body composition descriptive statistics are presented in Table 4, showing no significant differences between groups at baseline (p<0.05).

TABLE 4

Body compositional analysis of subjects (n = 60, 46♀ and 16♂) who completed the 24 week dietary intervention.

| | CON (n = 29; 24♀ and 5♂) | | | FORM (n = 31; 22♀ and 9♂) | | | |
|---|---|---|---|---|---|---|---|
| | Mean (SD) | Median (IQR) | Range | Mean (SD) | Median (IQR) | Range | P[1] |
| Age (y) | 59.5 (5.8) | 60.3 (11) | 50.8-69.5 | 62.2 (4.7) | 62.7 (6.8) | 53.4-69.8 | 0.054 |
| Height (cm) | 166.6 (5.9) | 165.7 (5.8) | 157.5-180.4 | 165.3 (7.7) | 162.7 (11) | 154.7-181.2 | 0.445 |
| BM (kg) | 71.9 (12.4) | 70 (18.8) | 51.7-104.3 | 70.6 (11.8) | 67.9 (20.5) | 51.3-95.1 | 0.666 |
| BMI (g/cm$^2$) | 25.9$^2$ (4.1) | 24.9 (5) | 18.9-37.0 | 25.7 (3.1) | 25.6 (4.3) | 20.0-33.7 | 0.871 |
| LTM (kg) | 43.8$^2$ (8) | 40.2 (7.3) | 36.8-66.3 | 44$^2$ (9.1) | 40.1 (17.3) | 33.3-60.8 | 0.510 |
| ALTM (kg) | 19.6$^2$ (4.1) | 18.0 (3.4) | 15.7-31.4 | 19.9$^2$ (4.7) | 17.8 (8.7) | 14.3-29.9 | 0.530 |
| Trunk LTM (kg) | 21.0$^2$ (3.7) | 19.9 (3.8) | 17.4-31.2 | 21.0$^2$ (4.2) | 19.6 (7.2) | 15.5-29.8 | 0.492 |
| Body Fat % | 35.2 (8.3) | 35 (10.6) | 17.0-48.5 | 34.2 (8.1) | 35.1 (12.6) | 10.7-45.7 | 0.631 |
| Total BMD | 1.193 (0.1) | 1.160 (0.2) | 1.025-1.426 | 1.132 (0.1) | 1.086 (0.2) | 0.871-1.431 | 0.070 |
| Spine BMD | 1.135 (0.2) | 1.105 (0.3) | 0.834-1.402 | 1.082 (0.1) | 1.079 (0.2) | 0.815-1.465 | 0.172 |
| Total Femur | 1.017 (0.2) | 0.991 (0.1) | 0.754-1.306 | 0.946 (0.1) | 0.902 (0.1) | 0.773-1.286 | 0.064 |
| Femoral Neck | 0.965 (0.1) | 0.937 (0.2) | 0.793-1.238 | 0.880 (0.1) | 0.853 (0.2) | 0.730-1.138 | 0.010 |
| CTx (ng/ml) | 0.379 (0.1) | 0.362 (0.2) | 0.118-0.651 | 0.332 (0.2) | 0.285 (0.2) | 0.063-0.811 | 0.268 |

[1]Independent T-Test/Mann Whitey U Test
[2]Non-normal distribution.
ALTMI, Appendicular lean tissue mass index;
BM, Body Mass;
BMD, Bone mineral density;
CON, Control group;
CTx; serum carboxy-terminal collagen crosslinks;
FORM, Formulation group;
IQR, Interquartile range;
LTM, Lean tissue mass;
LTMI, Lean tissue mass index;
SD, standard deviation Intervention Study A total of 60 of the 123 subjects (~50%) completed the study to 24 weeks, 29 CON (24 women, 5 men) and 31 FORM (22 women, 9 men). Reason for non-completion of the study were due to supplement palatability (n=27, 43%) (CON n=10; FORM n=17), not wishing to complete to 6 months (n=23, 37%), ill health unrelated to the intervention (n=6, 10%), relocation (n=3, 5%), time commitment (n=3, 5%) and personal circumstances (n=1).

Compliance to the supplement programme was monitored by monthly count-back of returned empty sachets and any remaining unused supplements. Compliance data pertaining to those subjects who completed 24 weeks of the supplementation programme is outlined in Table 5

TABLE 5

Compliance to dietary supplementation programme for participants who completed the 24 week intervention
CON (n = 29; 24♀ and 5♂), FORM (n = 31; 22♀ and 9♂)

|  | n | Mean |
|---|---|---|
| CON | 29 | 85% |
| FORM | 31 | 91% |
| ALL subjects | 60 | 88% |

Completion of a 4 day estimated food intake record (eFIR) and body compositional analysis preceded the 24 week intervention (0 weeks) and was repeated after 12 and 24 weeks of intervention. A registered dietitian gave oral and written instructions on recording food types, quantities, cooking methods and meal times. Participants were instructed to record all food and drink consumed for four consecutive days to include two week days and 2 weekend days, detailing information regarding the amount (using household measure and estimates of portion sizes), and types of all foods, beverages and nutritional supplements consumed over the recording period and where applicable, the cooking methods used, brand names of the foods consumed and details of recipes. Data were also collected on the time of each eating or drinking occasion.

Food intake data were coded and subsequently analysed using WISP© (Tinuviel Software, Anglesey, UK). WISP© uses data from McCance and Widdowson's The Composition of Foods, sixth (Food Standards Agency, 2002) to generate nutrient intake data. During this study, modifications were made to the food composition database to include recipes of composite dishes, nutritional supplements, generic Irish foods that were commonly consumed and new foods on the market. All previous modifications to the food composition database were also checked and updated from current manufacturers' information as necessary.

Analysis of nutrient intakes was carried out on mean daily nutrient intakes (MDI) and meal level analysis (MLA).

Figure 5:
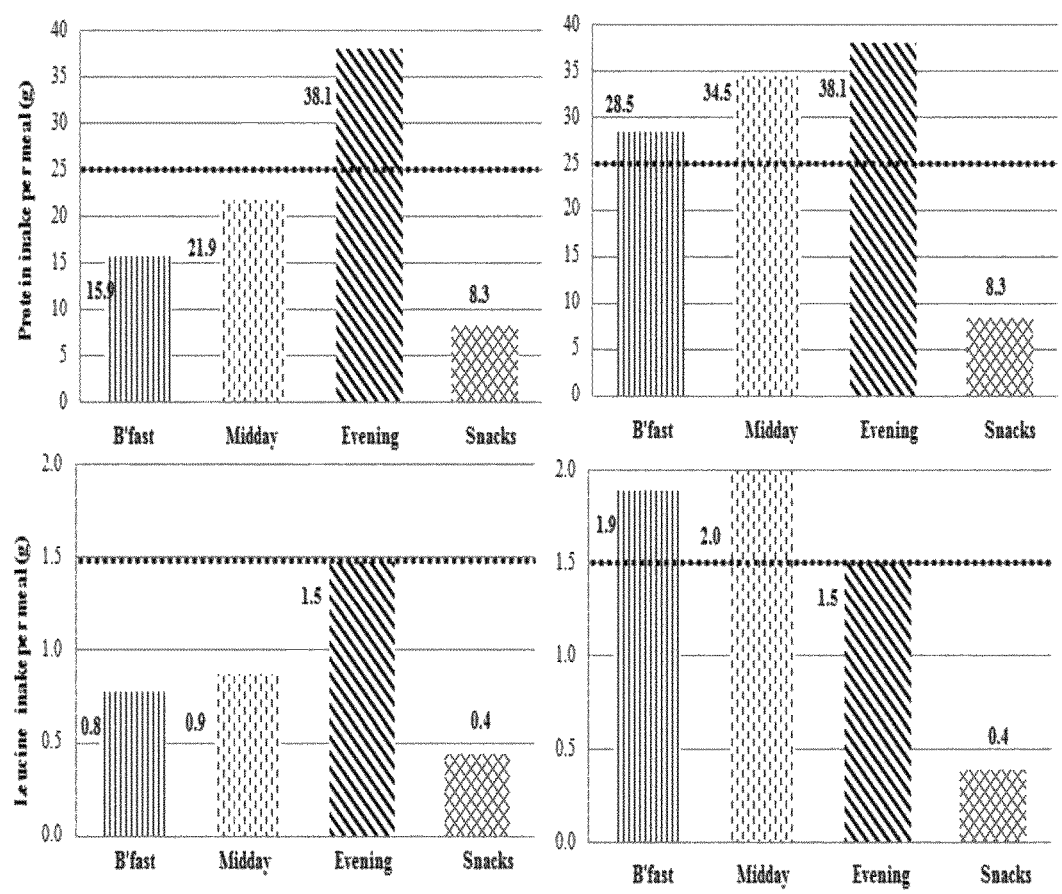
FIG. 5 Meal level analysis of protein and leucine intake per meal prior to (left) and optimised distribution following milk protein supplementation (right). Dashed line represents the proposed threshold for protein and leucine intake required to overcome "anabolic resistance" in older individuals (Paddon-Jones and Rasmussen, 2009).

Dietary Protein Intake;

A protein MDI of 1.2(0.3) $g \cdot kg^{-1} \cdot d^{-1}$ was 17(3) % of mean total energy intake (EI; 1981(406) $kcal \cdot d^{-1}$). All bar five subjects (96%) exceeded the RDA for protein intake (0.8 $g \cdot kg^{-1} \cdot d^{-1}$). The MLA of the reported daily nutrient intakes for protein and the key regulator of muscle protein synthesis, leucine, prior to, and following supplementation are presented in FIG. 5. Based on the extant literature suggested thresholds for protein and leucine intake required to overcome anabolic resistance in older individuals is projected within these data.

Lean Tissue Mass Change

The change in LTM for subjects who completed the 24 week intervention is presented in Table 6

At 24 weeks the mean LTM decreased by −0.16 (0.88) kg in the CON group compared to a mean increase of +0.45 (1.06) kg in the FORM group (ANOVA; P=0.006, 1−ß=0.87). Analysis of these data indicated a significant effect of treatment but not of gender (ANOVA; P=0.001 and P=0.688 respectively). A significant treatment×gender interaction was observed (ANOVA; P=0.013), indicating that the change in LTM was greater in males than in females. To ensure that any changes due to treatment were tested relative to the baseline, a two-way repeated measures ANCOVA confirmed these results (ANCOVA; P<0.001, ß=0.989).

Mean ΔLTM (%) decreased by −0.3 (2.1) % in the CON group compared to an increase of +0.91 (2.4) % in the FORM group (ANOVA; P=0.06, 143=0.861). The 1.2% mean difference in response between the treatment and control group was statistically significant (P=0.011), with no effect of gender or treatment×gender interaction (ANOVA; P=0.774 and P=0.092 respectively).

A significant difference in LTM was observed in the appendages (ALTM) with an increase of +0.07 (0.41) kg in the CON group compared to an increase of +0.27 (0.58) kg in the FORM group (ANOVA; P=0.002, 1−ß=0.92). A significant effect of treatment but not of gender was observed (ANOVA; P=0.007 and P=0.064 respectively). In the trunk, a decrease of −0.14 (0.6) kg in the CON group was observed compared to an increase of +0.21 (0.7) kg in the FORM group (ANOVA; P=0.07, 1−ß=0.587). The treatment effect was statistically significant (P=0.009), with no effect of gender or treatment×gender interaction (ANOVA; P=0.520 and P=0.085 respectively).

TABLE 6

Change (Δ) in LTM after 24 weeks of control (CON) or formulation (FORM) supplementation in 50-70 year olds

|  | Mean Δ (SD) | Range | P[1] |
|---|---|---|---|
| LTM (kg) |  |  |  |
| CON | −0.16 (0.9) | −1.94-1.44 |  |
| FORM | +0.45 (1.1) | −1.23-2.52 | 0.006 |
| LTM (%) |  |  |  |
| CON | −0.3 (2.1) | −4.44-3.62 |  |
| FORM | +0.91 (2.4) | −2.97-6.22 | 0.06 |
| ALTM (kg) |  |  |  |
| CON | +0.07 (0.41) | −0.92-0.71 |  |
| FORM | +0.27 (0.58) | −0.51-1.54 | 0.002 |
| Trunk LTM (kg) |  |  |  |
| CON | −0.14 (0.6) | −1.37-0.82 |  |
| FORM | +0.21 (0.7) | −0.89-1.87 | 0.07 |

[1]Two-way ANOVA corrected model with treatment group and gender as fixed factors
ALTM, Appendicular lean tissue mass;
CON, Control group;
FORM, Formulation group;
LTM, Lean tissue mass;
SD, standard deviation Bone Mineral Density and Bone Biomarker Change The change in BMD and biomarker of bone resorption (CTx) for subjects who completed the 24 week intervention is presented in Table 7.

At 24 weeks mean whole body BMD decreased by −0.73 (1.9) % in the CON group compared to a mean increase of +0.002 (1.8) % in the FORM group (ANOVA; P=0.499, 1−ß=0.21). There was no significant effect of treatment (P=0.466) or gender (P=0.367) or treatment×gender interaction (P=0.782). Similarly, no difference was observed at the femoral neck site (ANOVA; P=0.373, 1−ß=0.27), in treatment effect (P=0.891), gender (P=0.731) or treatment× gender interaction (P=0.131).

A statistically significant difference was observed at the total femur site, with a decrease of −0.25 (1.5) % in the CON group compared to an increase of +0.87 (1.5) % in the FORM group (ANOVA; P=0.046, 143=0.65), and no effect of gender (P=0.651), treatment (P=0.062) or interaction (P=0.524). A statistically significant difference was also observed at the lumbar spine, with a decrease of −0.94 (2.6) % in the CON group compared to an increase of +0.61 (3.1) % in the FORM group, i.e. BMD was greater in men vs. women independent of treatment group. (ANOVA; P=0.012, 1−ß=0.81). Analysis of these data showed a significant effect of gender (P=0.009) but not of treatment or gender×treatment interaction (ANOVA; P=0.209 and P=0.815 respectively).

TABLE 7

Change (Δ) in BMD and CTx after 24 weeks of formulation (FORM) or control (CON) supplementation in 50-70 year olds

|  | Mean Δ (SD) | Mean % Δ (SD) | Range | $P^1$ | $P^2$ |
|---|---|---|---|---|---|
| Whole Body (g/cm$^2$) | | | | | |
| CON | −0.007 (0.02) | −0.734 (1.9) | −4.4-3.9 | | |
| FORM | −0.0001 (0.02) | +0.002 (1.8) | −4.1-2.9 | 0.487 | 0.499 |
| Femoral Neck (g/cm$^2$) | | | | | |
| CON | 0.005 (0.3) | 0.482 (2.6) | −3.8-7.3 | | |
| FORM | 0.01 (0.02) | 1.106 (2.6) | −4.5-6.3 | 0.225 | 0.373 |
| Total Femur (g/cm$^2$) | | | | | |
| CON | −0.003 (0.02) | −0.252 (1.5) | −3.9-2.4 | | |
| FORM | 0.009 (0.01) | 0.867 (1.5) | −3.4-2.9 | 0.029 | 0.046 |
| Spine L1-L4 (g/cm$^2$) | | | | | |
| CON | −0.009 (0.03) | −0.942 (2.6) | −5.4-3.5 | | |
| FORM | 0.008 (0.04) | 0.613 (3.1) | −5.9-6.7 | 0.018 | 0.012 |
| Serum CTx (ng/ml) | | | | | |
| CON | −0.055 (0.2) | −9.056 (49.9) | −61.5-137.0 | | |
| FORM | −0.059 (0.3) | 0.122 (54.6) | −71.3-160.3 | 0.652 | 0.198 |

[1]Two-way ANOVA corrected model with treatment group and gender as fixed factors − absolute change.
[2]Percentage change
CON, Control group;
CTx, serum carboxy-terminal collagen crosslinks;
FORM, Formulation group;
SD, standard deviation At 24 weeks the mean serum CTx decreased by −9.1 (49.9) % in the CON group compared to a mean increase of +0.1 (54.6) % in the FORM group (ANOVA; P=0.198, 1−ß=0.40). This change was below the least significant change of 30.2% in serum CTx as calculated previously (Rosen et al 2000). There was no significant effect of treatment (P=0.673) or gender (P=0.100) or treatment× gender interaction (P=0.480).

The invention claimed is:

1. A nutritional supplement suitable for increasing lean tissue mass in a mammal, the supplement comprising per 100 g dry weight at least 60 g of a protein component, 0.01 mg to 0.1 mg vitamin D, and 1 g to 5 g calcium, and in which the protein component comprises:
   50 g-60 g of a casein-based milk protein composition,
   5 g-15 g of a first hydrolysed whey-based milk protein composition having insulinotropic bioactivity; and
   4 g-8 g of a second hydrolysed whey-based milk protein composition having antioxidant bioactivity.

2. A nutritional supplement as claimed in claim 1, in which the protein component comprises:
   52 g-56 g of a casein-based milk protein composition,
   11.7 g-12.5 g of the first hydrolysed whey-based milk protein composition; and
   5.8 g-6.2 g of the second whey-based milk protein composition.

3. A nutritional supplement as claimed in claim 1 and comprising:
   60 g-80 g of the protein component;
   3 g-4 g calcium; and
   0.04 mg-0.07 mg vitamin D.

4. A nutritional supplement as claimed in claim 1 and comprising:
   67 g-73 g of the protein component;
   2.5 g-3 g calcium; and
   0.05 mg-0.06 mg vitamin D.

5. A nutritional supplement as claimed in claim 1, in which the casein-based milk protein composition is a milk protein concentrate.

6. A nutritional supplement as claimed in claim 1, in which the first hydrolysed whey-based milk protein composition having insulinotropic activity is enzymatically hydrolysed whey protein concentrate having a degree of hydrolysis of 30-35% DH.

7. A nutritional supplement as claimed in claim 1, in which the second hydrolysed whey-based milk protein composition having anti-oxidant activity is enzymatically hydrolysed whey protein isolate having a degree of hydrolysis of 42-47% DH.

8. A nutritional supplement composition as claimed in claim 1 in which the protein component has an essential amino acid content of at least 40 g/100 g protein.

9. A nutritional supplement according to claim 1, wherein the nutritional supplement is provided in the form of a single dose suitable for administration with a meal and the single dose comprises 8 g to 17 g of the protein component, 6 μg to 13 μg vitamin D, and 250 mg to 500 mg calcium.

10. A nutritional supplement as claimed in claim 1, wherein the nutritional supplement is provided in the form of a single dose suitable for administration with a meal, and the single dose comprises 8 g to 17 g of the protein component, 6 μg to 13 μg vitamin D, and 250 mg to 500 mg calcium, wherein the single dose is a powder in a sachet.

11. A nutritional supplement as claimed in claim 1, wherein the nutritional supplement is provided in the form of a single dose suitable for administration with a meal, and the single dose comprises 8 g to 17 g of the protein component, 6 μg to 13 μg vitamin D, and 250 mg to 500 mg calcium, wherein the single dose is a powder divided between two sachets, in which the sachets are provided as a single package unit with a tear line dividing the two sachets.

* * * * *